United States Patent [19]
Wright et al.

[11] Patent Number: 5,147,637
[45] Date of Patent: Sep. 15, 1992

[54] METHOD OF INHIBITING THE INFLUX OF LEUKOCYTES INTO ORGANS DURING SEPSIS OR OTHER TRAUMA

[75] Inventors: Samuel D. Wright; Elaine Tuomanen, both of New York, N.Y.

[73] Assignee: The Rockefeller University, New York, N.Y.

[21] Appl. No.: 331,450

[22] Filed: Mar. 31, 1989

Related U.S. Application Data

[63] Continuation-in-part of Ser. No. 204,037, Jun. 7, 1988, abandoned.

[51] Int. Cl.$^5$ ............ A61K 39/00; A61K 35/14; C12N 5/00
[52] U.S. Cl. ............ 424/85.8; 530/388.22; 530/388.7; 435/240.27
[58] Field of Search ............ 424/85.8; 530/387; 435/240.27

[56] References Cited

U.S. PATENT DOCUMENTS

| | | | |
|---|---|---|---|
| 4,686,100 | 8/1987 | Raffin et al. | 424/85 |
| 4,797,277 | 1/1989 | Arfors | 424/85.8 |
| 4,840,793 | 6/1989 | Todd, III et al. | 424/85.8 |
| 4,935,237 | 6/1990 | Todd, III et al. | 424/85.8 |

FOREIGN PATENT DOCUMENTS

WO88/06592 7/1988 PCT Int'l Appl.

OTHER PUBLICATIONS

Wright et al (Sep. 1983) Identification of the C3bc receptor . . . PNAS 80:5699–5703.
Fischer et al (Nov. 1986) Prevention of Graft Failure by an Anti HLFA . . . Lancet 8515:1058–1061.
Arfors et al (Jan. 1987) A Monoclonal Antibody to the Membrane Glycoprotein . . . Blood 69:338–340.
Simpson et al (Feb. 1988) Reduction of Experimental Canine . . . J. Clin. Invest. 81:624–629.
Ismail et al., Blood, 69, 1167–1174 (1987).
Price et al., J. Immunology, 139, 4174–4177 (1987).
Quagliarello et al., Abstracts of the 1987 ICAAC, 204 (1987).
Rosen et al., J. Exp. Med., 166, 1685–1701 (1987).
Sande et al., Ped. Infec. Dis. J., 6, 1143–1171 (1987).
Tuomanen et al., J. Infect. Dis., 155, 985–990 (1987).
Tuomanen et al., Am. Rev. Respir. Dis., 135, 869–874 (1987).
Ripley-Petzoldt et al., J. Infect. Dis., 157, 245–255 (1988).
Tauber et al., J. Infect. Dis., 157, 456–464 (1988).
Wright et al., Proc. Natl. Acad. Sci. USA, 85, 7734–7738 (1988).
Lo et al., J. Exp. Med., 169, 1779–1793 (1989).
Tuomanen et al., J. Exp. Med., 170, 959–968 (1989).
Tuomanen et al., J. Infect. Dis., 151, 535–540 (1985).
Quagliarello et al., J. Clin. Invest., 77, 1084–1095 (1986).

*Primary Examiner*—Christine M. Nucker
*Assistant Examiner*—David R. Preston
*Attorney, Agent, or Firm*—Klauber & Jackson

[57] ABSTRACT

The influx of leukocytes into the lung and other organs during sepsis or other infectious or non-infectious trauma can be inhibited by the administration of anti-CD18 monoclonal antibodies. Such inhibition results in a prevention and/or diminishment of organ damage in inflammations and especially in endotoxic shock and adult respiratory distress syndrome.

6 Claims, 3 Drawing Sheets

METHOD OF INHIBITING THE INFLUX OF LEUKOCYTES INTO ORGANS DURING SEPSIS OR OTHER TRAUMA

The invention described herein was made, in part, in the course of work under Research Grants AI22003 and HL32418 from the National Institutes of Health, USPHS.

This application is a continuation-in-part co-pending application No. U.S. patent application Ser. No. 204,037, filed June 7, 1988, now abandoned, which is incorporated herein by reference.

BACKGROUND OF THE INVENTION

Leukocytes, and especially polymorphonuclear (PMN) leukocytes, circulate in the blood and do not adhere to the endothelium (the cells lining the vessels). Upon the introduction of an infectious agent, fragments that result from the death of an infectious agent, or another inflammatory substance into nearby tissues, leukocytes, especially PMN, are induced to bind to the endothelium and then migrate into the tissues. Since PMN can recognize and kill many infectious agents, this is a protective mechanism. However, in many disease circumstances, such as sepsis and trauma, PMN react in an exaggerated and deleterious fashion. They may bind so avidly to endothelium as to occlude blood flow. Once in the tissues, they secrete proteases, reactive oxygen intermediates, and other toxic molecules which not only kill infectious agents, but also can result in extensive tissue damage. In addition, they release inflammatory mediators that alter vascular tone and permeability, and that recruit additional leukocytes to the site, thus perpetuating inflammation.

Two diseases in which PMN-mediated damage contributes to morbidity and mortality are endotoxic shock and adult respiratory distress syndrome. In both instances, the lung is a preferred organ for emigration of PMN, and lung damage can be severe enough to cause death.

Adult respiratory distress syndrome (ARDS) can result from both infectious and non-infectious causes; either results in similar pathology as a consequence of PMN emigration. In endotoxic shock associated with infection, the use of antibiotics magnifies the deleterious effects of inflammation. This is due to the mechanism by which such agents exert their anti-infective effects. For example, following the administration of a betalactam antibiotic (or other cell-wall directed antibiotic), the bacteria disintegrate due to lysis by the anti-infective agents. The resulting fragments of bacteria initiate a dramatically enhanced inflammatory response. See Tuomanen et al., *Am. Rev. Resoir. Dis.*, 135, 869–874 (1987). Earlier research has indicated that inhibition of this antibiotic-induced inflammation correlates with improved morbidity and mortality in the setting of meningitis, Tuomanen et al., *J. Infect. Dis.*, 155, 985–990 (1985) and Kadurugamuwa, Program and Abstracts of the 27th ICAA Meeting, p. 205 (1987). In pneumococcal meningitis, for instance, mortality can be directly correlated with the amount of meningeal inflammation, McAllister et al., *J. Infect. Dis.* 132, 355–360 (1975). Thus, a method of dampening inflammation during the course of therapy with an antibiotic would be advantageous in treating infections, particularly endotoxic shock and ARDS associated with infection.

In a similar fashion, a method of dampening the inflammation associated with ARDS of noninfectious origin would likewise be a useful therapeutic tool for physicians.

A molecule on the surface of PMN that mediates adhesion to endothelium has recently been defined. That molecule, CD18, is thought to mediate adhesion because (a) monoclonal antibodies against CD18 inhibit binding of PMN to endothelium in vitro, (b) injection of monoclonal antibodies against CD18 into rabbits prevents normal emigration of PMN in response to an inflammatory stimulus, (c) PMN from patients with a genetic defect in the expression of CD18 fail to bind to endothelial cells in vitro, and (d) the deficient patients fail to recruit PMN to sites of infection.

CD18 has been previously described as a receptor for the third component of complement, C3bi (Wright et al., *PNAS*, 80, 5699–5703 (1983). A single receptor thus functions in two capacities, i.e., to mediate the binding of polymorphonuclear leukocytes (PMN) to endothelial cells, and to C3bi-coated cells.

It is thus an object of the present invention to provide a method of inhibiting the influx of leukocytes and particularly polymorphonuclear (PMN) leukocytes into the lung and other organs during sepsis or other infectious or non-infectious trauma which comprises the administration of a therapeutic amount of an anti-CD18 monoclonal antibody or active fragment thereof to a patient in need of such therapy.

It is a further object of this invention to treat inflammation in the lung and other organs in patients having an inflammation caused by sepsis or other infectious or non-infectious trauma by administration of a therapeutic amount of an anti-CD18 monoclonal antibody or active fragment thereof, to a patient in need of such therapy.

Another object of the present invention is to afford a method of treating a patient afflicted with endotoxic shock or adult respiratory distress syndrome by administering a therapeutic amount of an anti-CD18 monoclonal antibody, whereby the amount of the influx of PMN into the lung is eliminated or greatly reduced.

It is a still further object of this invention to eliminate or reduce the influx of leukocytes, and particularly polymorphonuclear (PMN) leukocytes, into the lung and other organs of a patient wherein the patient is being administered an anti-infective agent for an infectious disease by administering a therapeutic amount of an anti-CD18 monoclonal antibody or an active fragment thereof prior to, concurrent with, or after, the administration of the anti-infective agent, thereby eliminating or reducing inflammation.

SUMMARY OF THE INVENTION

The present invention concerns a method of inhibiting the influx of leukocytes into the lung and other organs during sepsis or other infectious or non-infectious trauma by administering a therapeutic amount of an anti-CD18 monoclonal antibody or fragment thereof. Highly preferred anti-CD18 monoclonal antibodies are those selected from the group consisting of anti-CD18 mAb IB4 deposited under #HB 10164 with American Type Culture Collection, Rockville, Md. (hereinafter designated as IB4) and anti-CD18 mAb 60.3 (hereinafter designated as 60.3) and active fragments thereof. Additionally, this invention concerns a method of inhibiting the ingress of leukocytes into the lung or other organs in patients having endotoxic shock or adult respiratory distress syndrome of any cause by administration of a therapeutic amount of an anti-CD18 monoclonal antibody or fragment thereof to a patient in need of such therapy. Highly preferred anti-CD18 monoclonal antibodies are those selected from the group consisting of IB4 and 60.3 and active fragments thereof.

This invention also concerns a method of eliminating or reducing inflammation in a patient wherein the patient is being administered an anti-infective agent for an infectious disease which comprises the administration prior to, along with or after the anti-infective agent of a therapeutic amount of an anti-CD18 monoclonal antibody or fragment thereof. Preferred anti-CD18 monoclonal antibodies are those selected from the group consisting of IB4, and 60.3 and fragments thereof. Dosage forms combining an anti-infective agent and a therapeutic amount of the monoclonal antibody or fragment thereof are also described.

DETAILED DESCRIPTION OF THE INVENTION

Figure 1:
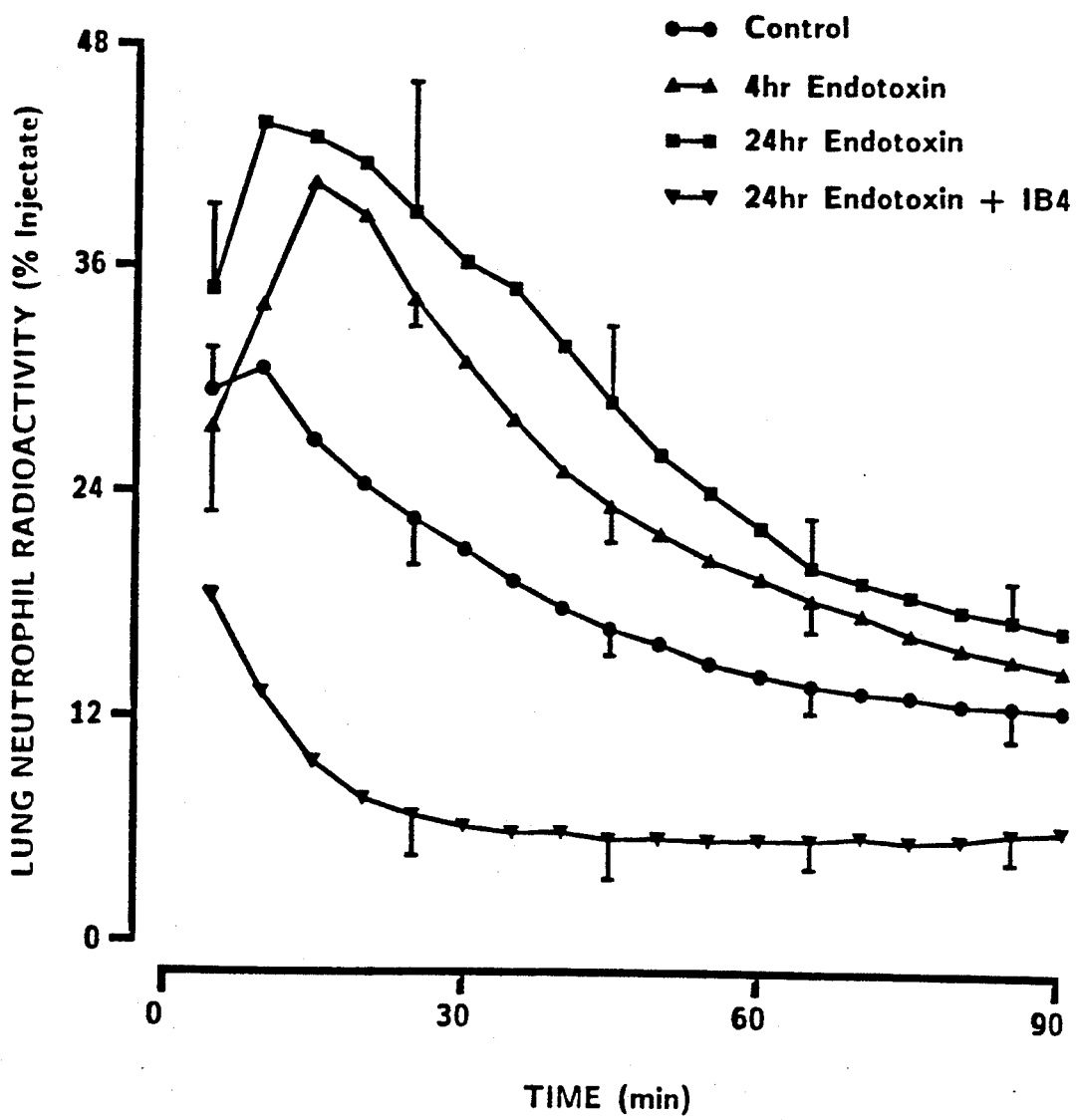
FIG. 1 is a graph showing the percentage of the injected neutrophil radioactivity in the lung versus time.

This invention relates to a method of inhibiting the influx of leukocytes into the lung and other organs during sepsis or other non-infectious trauma which comprises administration of a therapeutic amount of an anti-CD18 monoclonal antibody or active fragment thereof to a patient in need of such therapy.

The inflamed organ which is the target of the method of the present invention may result from any of a variety of infective agents, including gram-positive and gram-negative bacteria as well as viruses, parasites and fungi, or may arise from a noninfectious source such as trauma. Particularly targeted infections are those which are susceptible to treatment with beta-lactam antibiotics, such as *Haemophilus influenzae* B; *N. meninoitides* b; pneumococci, *Streptococcus pneumoniae; Escherichia coli; Staphylococcus epidermidus: Staphylococcus aureus:* group B Streptococci; Salmonella; *Bacillus subtillis;* and *Pseudomonas aeruginosa.*

The inflamed organ which is the target of the present invention can likewise be any body organ susceptible to inflammation by the above-described agents. The method of the present invention is, however, particularly adaptable to the treatment of the lung, central nervous system, kidney, joints, endocardium, eyes and ears, with the treatment of the lung being a highly preferred embodiment.

The method of the present invention has been found to be useful in preventing the ingress of leukocytes into the lung of mammals afflicted with sepsis. Such activity enables their preferred route of administration to be intravenous, and their administration to be particularly useful in the treatment of such infections, including those arising from pneumococci, *Haemoohilus influenzae* B, *N. meninoitides* b and *Escherichia coli.* group B Streptococcus, Staphylococci and Pseudomonas.

Similarly, the method of the present invention is also applicable to inflammation arising from causes other than infections, such as (acute respiratory distress syndrome) precipitated by burns, surgery, toxic chemicals, fracture of bones, or other trauma.

The particular anti-CD18 monoclonal antibodies which can be utilized in the practice of the methods of the present invention are preparable by standard techniques. Preferred monoclonal antibody IB4 is described in Wright et al., *Proc. Natl. Acad. Sci. USA,* 80, 5699-5703 (1983). Monoclonal antibody 60.3, another preferred embodiment, is described in Beatty, et al., *J. Immunology.* 131, 2913-2918 (1983).

Other anti-CD18 monoclonal antibodies, as well as methods for their preparation, are described in "Leukocyte Typing III", Springer-Verlag, N.Y. (1988).

In certain patients, a potential problem with the use of the murine monoclonal antibody, such as IB4 or 60.3, may exist since the patient may generate an immune response against a murine monoclonal antibody. This effect may be ameliorated or obviated by using active fragments of the monoclonal ahtibody so as to minimize the amount of foreign protein injected. Another alternative is to employ genetic engineering techniques to make a chimeric antibody in which the binding region of the murine antibody IB4 or 60.3 is combined with the constant regions of human immunoglobulin.

A further method of the present invention is that of reducing or eliminating the influx of leukocytes into the lung in endotoxic shock or adult respiratory distress syndrome associated with the administration of an anti-infective agent. The method comprises the administration prior to, along with, or after the anti-infective agent of a therapeutic amount of an anti-CD18 monoclonal antibody or an active fragment thereof to a patient in need of such therapy. Preferred anti-CD18 monoclonal antibodies are IB4 and 60.3. Due to the mechanism of their therapeutic activity, anti-infective agents, and particularly beta-lactam antibiotics, cause additional inflammation as a result of their therapeutic effect. Although such anti-infective agents sterilize a given infection, they cause release of toxic products, for example, the cell wall and/or endotoxin of the infecting agent. Such bacterial components initiate an inflammatory response, often most acute in the lung. It is this inflammation which contributes significantly to the lung damage that is the long-term consequence of many infections.

Reduction or elimination of inflammation in inflammatory diseases, particularly endotoxic shock and adult respiratory distress syndrome, results in a diminution of the organ damage that usually accompanies such disease states. Since the monoclonal antibodies IB4 and 60.3 possess the unique ability to block movement of leukocytes into the lung and other organs, they are uniquely suited to treat both non-infectious causes and infectious causes. Causative infective agents are those such as *Haemophilus influenza* B, *N. meningitides* b, *E. coli, Staphylococci,* or a pneumococci such as *Streptococcus pneumoniae.* Such infections are generally treated with an aminoglycoside such as gentamicin or a beta-lactam antibiotic such as a penicillin or cephalosporin. Among the typically utilized aminoglycosides, penicillins and cephalosporins used in the treatment of such infections are cephalothin, cephaloridine, carbenicillin, ampicillin, nafcillin sodium, cloxacillin, dicloxacillin, oxacillin, methicillin sodium, phenoxymethyl penicillin, procaine penicillin G, benzathine penicillin G, penicillin G, cephacetrile sodium, cephalexin, cephapirin sodium, cephradine, penicillin V, gentamicin, kanamycin, chloramphenicol, cefotaxime, ceftriaxione, vancomycin, and imipenem.

Due to the ability of the anti-CD18 monoclonal antibodies to reduce or eliminate the influx of leukocytes into the lung and other organs in a infectious disease caused by the administration of an anti-infective agent, the anti-CD18 monoclonal antibody or active fragment thereof can be combined in a single unit dosage form with the anti-infective agent for convenience of administration. Such dosage form is most preferably an intravenous dosage form since most anti-infective agents, particularly the beta-lactam antibiotics, are available in a suitable chemical form for administration via the intravenous route. This is also the preferred route of administration for the monoclonal antibodies, such as IB4 and 60.3. Typically, the anti-infective agent and the monoclonal antibody can be combined in a single ampoule solution. Where this is not possible, the anti-infective agent and the monoclonal antibody can be packaged separately and mixed just prior to injection. Administration can likewise be via a mixture with any standard intravenous solution, i.e., normal saline.

The amount of anti-infective agent in the dosage form is dependent upon the particular anti-infective agent being utilized and the particular infection being treated. The amount of the monoclonal antibody utilized in a dosage form can range from about 1 to about 1,000 mg, with 10–100 mg per dosage unit being highly preferred. Dosages can be administered one to four times daily, with continued therapy for as long as the infection persists.

The method of administering the dosage unit may, of course, be varied by the treating physician due to patient condition and the severity of the infectious disease being treated.

The following examples illustrate the methods and preparations of the present invention.

EXAMPLE 1

Inhibition of Leukocytes in the Lung

Rabbit Neutrophil Isolation

New Zealand White Rabbits (2–3 kg) are given 60 mg/kg of sodium Pentobarbital. Through a cardiac puncture, 60 ml of blood is obtained into a heparinized syringe. The blood is centrifuged at 400 xg for 20 minutes and the platelet-rich plasma is removed. The platelet rich plasma is centrifuged at 2500 xg for 15 minutes to provide a source of autologous platelet-poor plasma. Eight ml of 6% dextran 500 in saline is added to the red cell pellet and normal saline is added to bring the volume up to 50 ml. The red cells are allowed to sediment for 30–60 minutes and the leukocyte-rich plasma is aspirated. The neutrophils are separated from leukocytes by centrifugation over discontinuous Percoll-plasma gradients (43% over 53%). The neutrophils are pelleted and the remaining red blood cells are removed with distilled water lysis. All reagents used for neutrophil isolation procedure are tested for the presence of endotoxin using the limulus lysate assay and are not used if any contamination is found. Similarly, all laboratory ware that is used is endotoxin-free.

Preparation of IB4 Antibody

The antibody to the CDllb/CD18 receptor is prepared by the method described in *Proc. Natl. Acad. Sci. USA*, 80, 5699–5703 (1983). The antibody is obtained from mouse ascites fluid and is purified by affinity chromatography to remove all non-immunoglobulin proteins.

Neutrophil-Labeling

Neutrophils are labelled with $^{111}$In. Tropolone (4 mM in normal saline) was added at equal volume to the $^{111}$In chloride (Amersham). The $^{111}$-In-tropolone is added dropwise to neutrophils suspended in autologous plasma. Neutrophils are allowed to incubate for 30 minutes at room temperature and are then washed with autologous plasma. Neutrophils are labelled with this technique generally with greater than 60% labelling efficiency. Isolated and labelled neutrophils are tested for chemotaxis to opsonized zymosan and adherence into bovine pulmonary artery endothelial monolayers induced by phorbol myristate acetate. The neutrophils show normal chemotaxis and normal adherence. In addition, the PMA-induced adherence of rabbit neutrophils to bovine pulmonary vascular endothelium could be inhibited by pretreatment with IB4.

Experimental Protocol

Rabbits are placed into a plastic restraining cage and placed on a large field of view gamma-camera (Dymax, ElScint, Haifa, Israel). The camera is fitted with a medium energy, medium resolution parallel hole collimator. An intravenous line is placed into a marginal ear vein and an arterial line is placed into the central ear artery of the rabbit. The rabbit is infused with the labelled neutrophils and dynamic 5 minute gamma camera images are obtained for 4 hours. Arterial blood samples are obtained every 15 minutes through the 4-hour period. Control rabbits are not given and pretreatment. One group of rabbits is treated 4 hours before imaging with *E. Coli* endotoxin (100 μg). Another group is treated with endotoxin 24 hours prior to imaging and is given IB4 antibody (0.5 mg/kg) 20 minutes prior to imaging. Another group of animals received no endotoxin treatment, but are treated with IB4 antibody 20 minutes prior to imaging.

Data Analysis

Regions of interest are drawn around the lungs, liver, spleen and the whole body of the rabbits. The counts within these regions of interest are summed to produce sum activity curves. The counts in the lung, liver and spleen are expressed as fractions of the activity within the entire rabbits' body. The activity in the blood samples is expressed as counts per minute/gm of blood and are also expressed as a fraction of circulating activity relative to the total injected activity. The significance of differences between groups is determined by analysis of variance and student's T test where appropriate. The lung data are modeled to a two-compartment exponential wash-out equation.

Results

The fraction of the injected neutrophil radioactivity in the lung versus time is shown in FIG. 1. Control animals show a rapid wash-out from the lung with tracer activity in the lung reaching 13% by 90 minutes. The peak amount of activity in the lungs of the control rabbits is 31%. In animals treated with endotoxin 4 hours prior to study, the peak amount of activity in the lungs is 41% and the wash-out from the lungs is slower, with 16% of the neutrophil radioactivity remaining in the lung at 90 minutes. With 24 hour pretreatment with endotoxin, an even greater response is seen with about 44% of the neutrophils initially localizing in the lung and with a 90-minute wash-out of 18%. When animals are given the endotoxin 24 hours before study and given IB4 20 minutes before study, the peak activity in the lung (18%) is less than both control and the 24-hour endotoxin treatment group. The wash-out is faster and 6% of the neutrophil radioactivity remained in the lungs at 90 minutes. These data indicate that IB4 prevents sequestration of PMN into the lung after endotoxin-induced lung injury.

Blood Data

Figure 2:
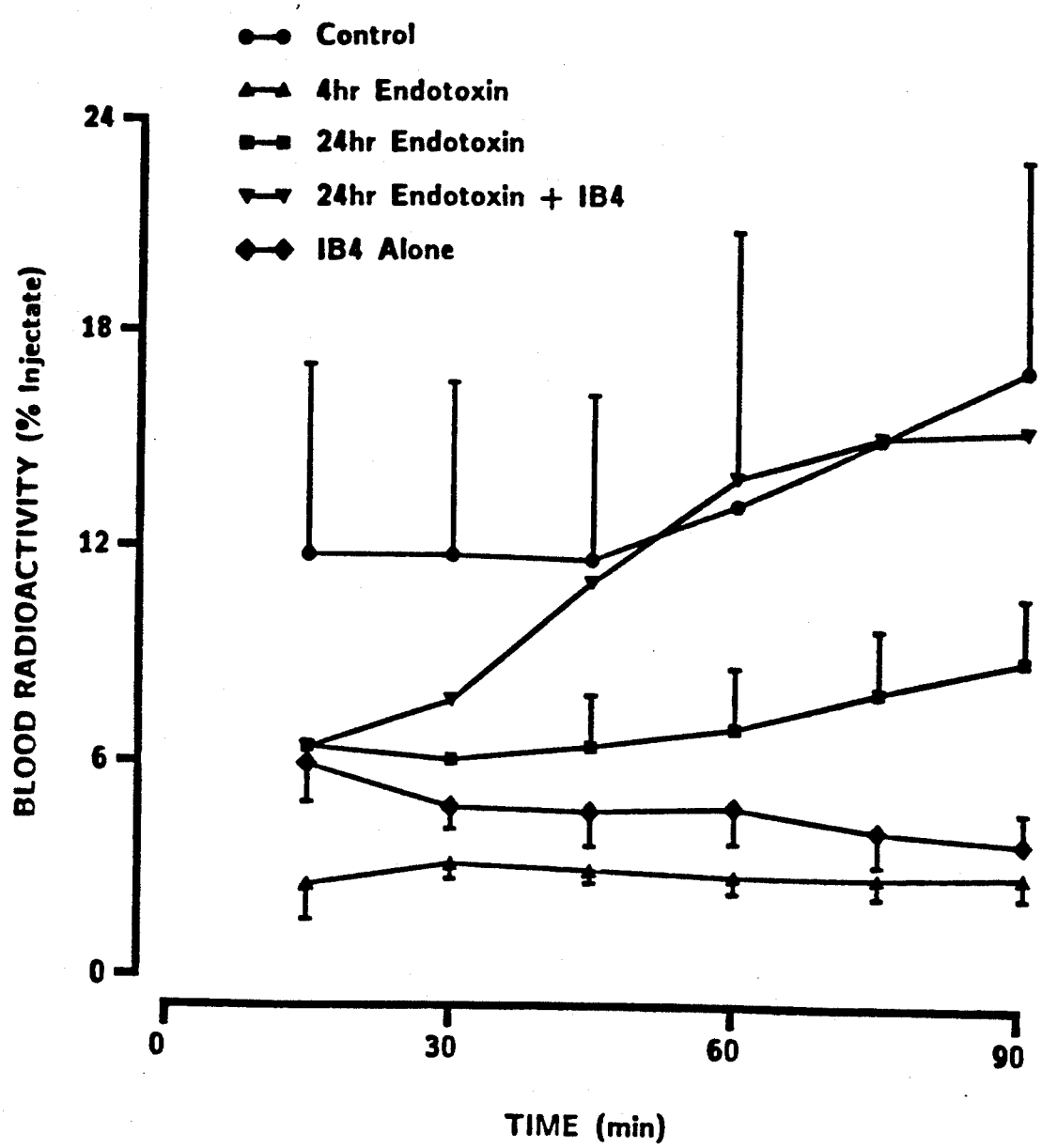
FIG. 2 is a graph showing the neutrophil radioactivity in the blood versus time. The circulating radioactivity is expressed as a percent of the total injected radioactivity.
Figure 3:
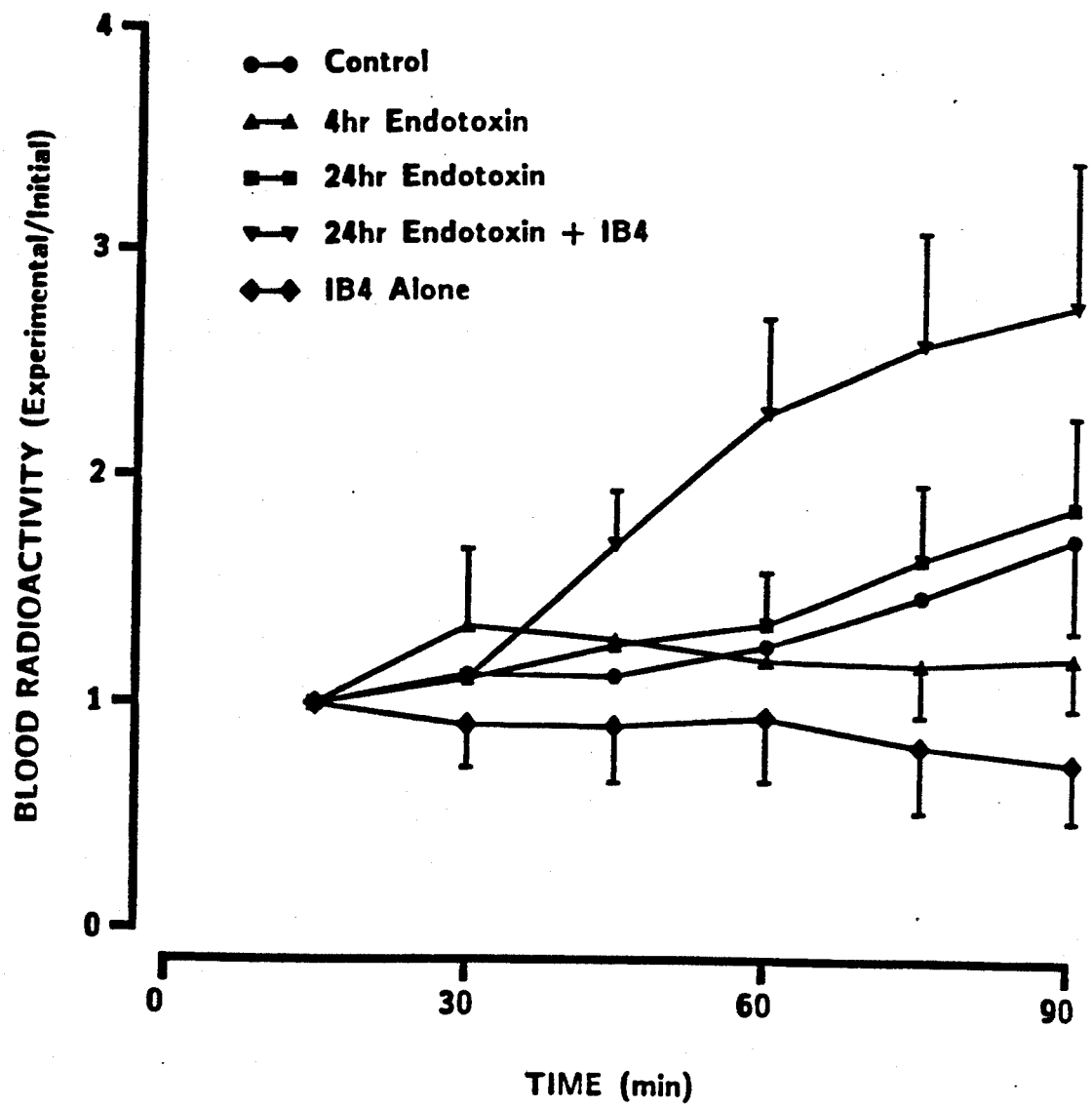
FIG. 3 is a graph showing neutrophil radioactivity in the blood versus time. The circulating radioactivity is expressed as a ratio to the initial 15-minute value.

The blood radioactivity is expressed as a fraction of the experimental value to the 15-minute baseline value (see FIG. 2). The control group shows a small rise in blood radioactivity over time, which likely represents wash-out from neutrophils sequestered in the lung. The 4-hour endotoxin group also shows a slight rise over time, very similar to the control group. The 24-hour endotoxin group shows a large increase in the blood radioactivity over time. The 24-hour endotoxin group, which was also treated with IB4, showed the most rapid rise in blood radioactivity which stabilizes at about 80 minutes and then gradually falls. The rate of uptake in the 24-hour endotoxin and IB4-treated group appears to be somewhat faster than that seen in the 24-hour endotoxin alone treatment group. The blood data expressed as a fraction of the infused neutrophils that are in circulation are shown in FIG. 3. Control neutrophils show a slight rise over time with about 20-30% of neutrophils circulating after infusion. The 4-hour endotoxin group also shows a stable amount but with about 3% of neutrophils circulating during this study. The 24-hour endotoxin group also shows a stable or gradually rising amount of radioactivity over time with about 8-12% of neutrophils circulating during the course of the study. The group treated with 24 hours of endotoxin and then IB4 shows a pattern that is similar to the 24-hour endotoxin treatement group with an initial rise and then a gradual plateau with circulating fractions between 3 and 8%. These data indicate that the mechanism by which IB 4 inhibits sequestration of PMN into the lung is not due to clearance of the PMN by the reticuloendothelial system.

EXAMPLE 2

Formulations

| EXAMPLE 2 Formulations | |
|---|---|
| Ingredient | mg/ml |
| Intravenous Formulation I | |
| cefotaxime | 250.0 |
| monoclonal antibody IB4 | 10.0 |
| dextrose USP | 45.0 |
| sodium bisulfite USP | 3.2 |
| edetate disodium USP | 0.10 |
| water for injection q.s.a.d. | 1.00 ml |
| Intravenous Formulation II | |
| ampicillin | 250.0 |
| monoclonal antibody 60.3 | 10.0 |
| sodium bisulfite USP | 3.2 |
| disodium edetate USP | 0.1 |
| water for injection q.s.a.d. | 1.00 ml |
| Intravenous Formulation III | |
| gentamicin (charged as sulfate) | 40.0 |
| monoclonal antibody IB4 | 10.0 |
| sodium bisulfite USP | 3.2 |
| disodium edetate USP | 0.1 |
| water for injection q.s.a.d. | 1.00 ml |
| Intravenous Formulation IV | |
| monoclonal antibody IB4 | 10.0 |
| dextrose USP | 45.0 |
| sodium bisulfite USP | 3.2 |
| edetate disodium USP | 0.10 |
| water for injection q.s.a.d. | 1.00 ml |
| Intravenous Formulation V | |
| monoclonal antibody 60.3 | 10.0 |
| sodium bisulfite USP | 3.2 |
| disodium edetate USP | 0.1 |
| water for injection q.s.a.d. | 1.00 ml |

As indicated earlier, the present invention is applicable to the treatment of a variety of inflammatory disease states including infectious diseases where active infection exists at any body site, such as in the instance of meningitis. Also included are conditions such as secondary inflammations whether acute or chronic, that may occur at a site of antigen deposition that is secondary to a primary infection at a distant body site, and exemplary specific conditions would also include meningitis, as well as encephalitis, arthritis, uveitis, colitis, such as inflammatory bowel/Crohn's disease, glomerulonephritis, dermatitis, and psoriasis. Also included is the inflammation that results from alterations in leukocyte movement during infection such as adult respiratory distress syndrome associated with sepsis.

Other inflammatory disease states include immune disorders and conditions involving T-cell and/or macrophage attachment/recognition; such as, acute and delayed hypersensitivity, graft vs. host disease; primary auto-immune conditions such as pernicious anemia; infection related autoimmune conditions such as Type I diabetes mellitus; flares during rheumatoid arthritis; diseases that involve leukocyte diapedesis, such as multiple sclerosis; antigen-antibody complex mediated diseases including certain of the secondary infection states listed above; immunosuppression; and transplant rejection. Inflammation due to toxic shock or trauma such as adult respiratory distress syndrome and reperfusion injury; and that which is due to tumorous conditions such as leukocyte dyscrasias and metastasis, is likewise included within the scope hereof.

In addition to the above, the present invention is applicable to the inhibition of leukocyte-endothelial attachment in the instances of non-disease states and in particular, for diagnostic and therapeutic purposes; such as the iatrogenic opening of the endothelium to prevent the ingress leukocytes during the ingress of a dye or image enhancer into tissue, or to allow the selective entry of a therapeutic drug in the instance of chemotherapy; or to enhance the harvesting of leukocytes from patients.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method substantially reducing inflammation associated with the disease state of meningitis or encephalitis in a patient in need of such therapy wherein the patient is being administered an anti-infective agent which comprises the administering of a therapeutic amount of an anti-CD18 monoclonal antibody or active fragments thereof, in a pharmaceutically acceptable carrier, prior to, concurrent with, or after, the administration of the anti-infective agent, to said patient.

2. A method according to claim 1 wherein the anti-CD18 monoclonal antibody is anti-CD18 mAb IB4.

3. A method according to claim 1 wherein the anti-CD18 monoclonal antibody is anti-CD18 mAb 60.3.

4. A method according to claim 1 wherein the anti-infective agent is a beta-lectam antibiotic.

5. A method according to claim 1 wherein the antibody or fragment thereof is administered intravenously.

6. A method according to claim 1 wherein the inflammation results from endotoxic shock.

* * * * *